United States Patent
Spears

(10) Patent No.: US 11,654,205 B2
(45) Date of Patent: May 23, 2023

(54) SYSTEM AND METHOD TO CONTROL NUCLEATION OF BUBBLES

(71) Applicant: OAKWOOD HEALTHCARE, INC., Dearborn, MI (US)

(72) Inventor: James Richard Spears, Bloomfield Hills, MI (US)

(73) Assignee: Oakwood Healthcare, Inc., Dearborn, MI (US)

( * ) Notice: Subject to any disclaimer, the term of this patent is extended or adjusted under 35 U.S.C. 154(b) by 146 days.

(21) Appl. No.: 16/754,986

(22) PCT Filed: Oct. 9, 2018

(86) PCT No.: PCT/US2018/055047
§ 371 (c)(1),
(2) Date: Apr. 9, 2020

(87) PCT Pub. No.: WO2019/074947
PCT Pub. Date: Apr. 18, 2019

(65) Prior Publication Data
US 2021/0205480 A1 Jul. 8, 2021

Related U.S. Application Data

(60) Provisional application No. 62/570,311, filed on Oct. 10, 2017.

(51) Int. Cl.
| | | |
|---|---|---|
| *A61B 8/00* | (2006.01) | |
| *A61K 49/22* | (2006.01) | |
| *A61M 5/00* | (2006.01) | |
| *B01F 23/232* | (2022.01) | |
| *A61B 8/08* | (2006.01) | |
| *B01F 25/00* | (2022.01) | |
| *B01F 101/00* | (2022.01) | |

(52) U.S. Cl.
CPC ........... *A61K 49/223* (2013.01); *A61M 5/007* (2013.01); *B01F 23/232* (2022.01); *A61B 8/481* (2013.01); *B01F 2025/917* (2022.01); *B01F 2025/9321* (2022.01); *B01F 2101/2202* (2022.01)

(58) Field of Classification Search
CPC ................. A61K 49/223; B01F 23/232; B01F 2025/917; B01F 2025/9321; B01F 2101/2202; A61M 5/007; A61B 8/481
See application file for complete search history.

(56) References Cited

U.S. PATENT DOCUMENTS

| | | | |
|---|---|---|---|
| 7,525,108 B2 | 4/2009 | Tomimatsu et al. | |
| 9,724,460 B2 * | 8/2017 | Spears | ................. B65D 83/303 |
| 10,898,637 B2 * | 1/2021 | Spears | ................. A61M 13/003 |
| 11,047,053 B1 * | 6/2021 | Anderson | ............. C25B 11/042 |
| 2002/0009015 A1 * | 1/2002 | Laugharn, Jr. | .......... B01F 35/71 |
| | | | 366/108 |
| 2004/0253183 A1 | 12/2004 | Uber et al. | |
| 2015/0273134 A1 | 10/2015 | Spears | |

OTHER PUBLICATIONS

Ali et al. (Int. J. Precis. Eng. Manuf. 11, 157-170 (2010)).*
International Preliminary Report on Patentability dated Apr. 23, 2020 in corresponding/related International Application No. PCT/US2018/055047.
International Search Report and Written Opinion of the International Searching Authority issued in PCT/US2018/055047, dated Dec. 31, 2018; ISA/US.

* cited by examiner

*Primary Examiner* — Michael G. Hartley
*Assistant Examiner* — Melissa J Perreira
(74) *Attorney, Agent, or Firm* — Harness, Dickey & Pierce, P.L.C.

(57) ABSTRACT

Generation of bubbles is disclosed to occur within a flow of an aqueous fluid. The bubbles may be formed within a tube of a selected diameter and the bubbles are controlled to exit the tube at a selected diameter. Generally, bubbles are formed to include a diameter of less than 1 millimeter, including less than about 20 microns.

20 Claims, 3 Drawing Sheets

SYSTEM AND METHOD TO CONTROL NUCLEATION OF BUBBLES

CROSS-REFERENCE TO RELATED APPLICATIONS

This application is the U.S. National Phase Application under 35 U.S.C. 371 of International Application No. PCT/US2018/055047 filed on Oct. 9, 2018, which claims the benefit of U.S. Provisional Application No. 62/570,311, filed Oct. 10, 2017. The entire disclosures of the above applications are incorporated herein by reference.

FIELD

The present disclosure relates to nucleation of bubbles in an aqueous flow, and particularly to a controlled nucleation and bubble size within a tube.

BACKGROUND

This section provides background information related to the present disclosure which is not necessarily prior art.

Providing bubbles to a volume, such as a human subject or other appropriate aqueous filled volume, can be used for various procedures. In some examples, providing a volume of bubbles to a subject can be useful as an echogenic contrast agent. Bubbles may be created by the agitation of a solution, such as saline, by reciprocating connected syringes and injecting the resultant bubbles into a volume. For example, agitated air in saline and agitated air in blood and saline mixtures can generate bubbles that are introduced intravenously. Agitation methods can generate bubbles in the range of 26 µm to 32 µm, as disclosed in Doo-Soo Jeon, M. D. et al., "The usefulness of a 10% air-10% blood-80% saline mixture for contrast in echocardiography, Doppler Measurement of Pulmonary Artery Cystolic Pressure", J Am Coll Cardiol, 39:1, p. 124 129 (January 2002).

Generating bubbles, especially in a selected volume, of a selected small size is difficult. A nucleation site may be generated with a deposition of a selected material, such as a gallium or a gallium alloy, such deposition generally occurs by dipping or painting of liquid gallium to a substrate. In particular, with a tube or pipe having a small internal diameter, such as about 100 micrometers (microns), deposition is difficult and imprecise. For example, the deposition of the gallium or gallium alloy may be substantially limited to a selected region essentially at a tip of the tube.

SUMMARY

This section provides a general summary of the disclosure, and is not a comprehensive disclosure of its full scope or all of its features.

Delivery of bubbles to a selected volume may enhance a selected procedure. For example, certain imaging techniques may require or be enhanced by the use of a contrast agent. A plurality of bubbles, for example, of a selected size, can be positioned in the volume to enhance echogenic contrast within the volume. The generation of bubbles can be formed in various manners, such as generation of gas bubbles from one or more nucleation sites in a flow of a liquid.

The bubbles may be generated or nucleated on a surface from gas dissolved in a fluid. The fluid may be a liquid and may be referred to as a carrier liquid. The carrier liquid is saturated with a selected gas at a selected level of pressure in a container. The selected gas can include oxygen, such as gaseous and molecular oxygen. The oxygen gas may be substantially pure and/or sterile. Pure oxygen may be oxygen gas that is generally provided for use in a medical procedure and appropriate for injection into a vascular system of a human subject. The liquid can include any appropriate liquid, such as sterile saline, lactated ringer, 5% dextrose saline, or other sterile materials.

A delivery tube, such as one formed of fused silica, can be interconnected with the container to allow delivery of the carrier liquid that is saturated with the gas at a selected rate. The tube may have a selected internal diameter (i.d.) such as about 1 micrometers (microns) to about 2 millimeter (mm), including about 20 microns to about 200 microns, and further including about 50 microns to about 100 microns. The tube, such as the internal surface that forms the tube defines at least a portion of the i.d. that may be augmented with a selected material and/or process.

The tube may include a substantially smooth internal surface that forms or defines the internal diameter. The internal surface may be initially free of any regions or portions that may include imperfections including pits, crevices, or the like. The smooth tube having the smooth internal surface initially free to defects includes defects of less than about 10 nanometers (nm) to about 100 (nm), including about 50 nm. Formation of selected nucleation sites, including sub- or below surface portions including pits or crevices, may be formed in the inner surface of the tube using a selected process such as focused ion beam (FIB). Selected tubing, including tubing formed of fused silica, may be formed free of surface imperfections, as discussed above. The FIB is used to form pits or crevices on the inner surface of the tube on the size of about 0.01 nanometers (nm) to about five microns and further including about 0.05 microns to about 1.0 microns.

The formed pits or crevices provide nucleation sites for formation of bubbles in a flow of a gas-supersaturated fluid flowing through the tube. A relatively low Reynold's numbers associated with selected tubing, such as a silica capillary tubing, allow flow to remain substantially laminar at relatively high velocities (e.g. about 10 meters per second (m/s) to 30 m/s) compared to ordinary pipe flow Reynold's numbers. The high laminar flow velocities of gas-supersaturated fluid through such capillaries effectively shear off bubbles at selected sizes, for example bubbles having an average size range of a few nanometers to several micrometers, such as about 0.01 microns to about 10 microns in diameter (also herein referred to as micronanobubbles) nucleating from formed nucleation sites at an early stage of bubble growth. Even when high levels of gas supersaturation in the flowing fluid are required to initiate bubble nucleation from formed nucleation sites (for example, pressure ranges of about 8 bars (116 psi) to about 30 bars (435 psi) for oxygen), ejection of the sheared-off bubbles from the distal end of the tubing into host fluid having a lower gas concentration inhibits further growth of the bubbles. The high flow rate of the fluid may ensure or generate small bubbles as they are sheared soon after bubble nucleation and formation begins. Thus, efficient delivery of bubbles, including a large number of bubbles, having a diameter at or less than one micron in diameter may occur into a host liquid under laminar flow conditions may occur.

Moreover, various deposition techniques may deposit selected materials on the i.d. in addition to sputtering the surface of the tube to form selected nucleation sites (e.g. pits or crevices). The deposition of material may include the deposition of gallium or gallium ions on or in the surface of the i.d. of the tube. The deposition of the selected material may form amorphous sites for selected nucleation site for bubbles.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

Corresponding reference numerals indicate corresponding parts throughout the several views of the drawings.

DETAILED DESCRIPTION

Example embodiments will now be described more fully with reference to the accompanying drawings.

Figure 1:
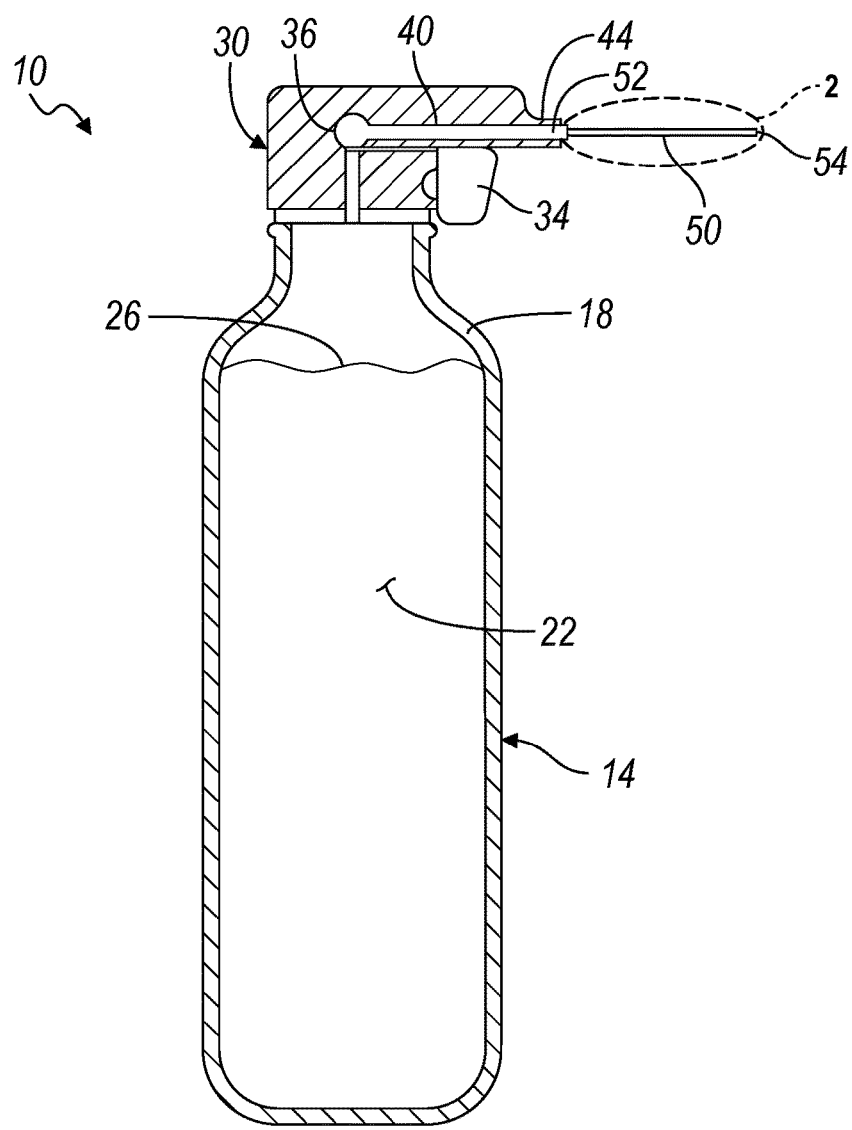
FIG. 1 is a cross-section view of a container, according to various embodiments.

According to various embodiments, a delivery system 10 is illustrated in FIG. 1. The delivery system 10 is provided to deliver a material to a subject, such as a living or non-living subject. The subject may either be a living subject or a non-living subject that defines a volume. The material from the delivery system 10 may be delivered to the volume for various purposes, such as providing a volume or number of bubbles in a selected size to the volume. The volume may include, for example, a heart chamber, a fluid-filled container or volume for a mechanical construct, or other appropriate subject.

The delivery system 10 includes a container 14 that has a wall 18 that contains or defines a volume 22. The volume 22 may be filled with a delivery fluid, as discussed further herein to a selected amount. The delivery fluid 26 may be any appropriate fluid, such as an aqueous fluid that is contained under pressure within the container 14. A selected actuation mechanism, such as a trigger or nozzle mechanism 30 is connected to the container 14 to allow for delivery of a selected portion of the delivery fluid 26 to a selected location, as also discussed further herein. The trigger mechanism 30 may include a manual or automatic trigger 34 that operates a valve 36. The trigger 34 may be moved or depressed to open the valve 36. The trigger 43 may be further biased such that releasing the trigger 34 may close the valve 36 with no further action from the user. The trigger 34 and the valve 36 may be of appropriate configurations that are able to maintain the delivery fluid 26 within the container 14 at the selected pressures, as discussed further herein.

The trigger mechanism 30 may further include an initial passage 40 that extends from the valve 36 to a region of the trigger mechanism 30, such as a nozzle or nose 44. Connected or extending from the nozzle 44 is a delivery tube 50. The delivery tube extends from a proximal end 52 generally connected to or attached to the nozzle 44 to a distal end 54 that may be a terminal distal end 54 and an exit of the tube 50.

Figure 2:
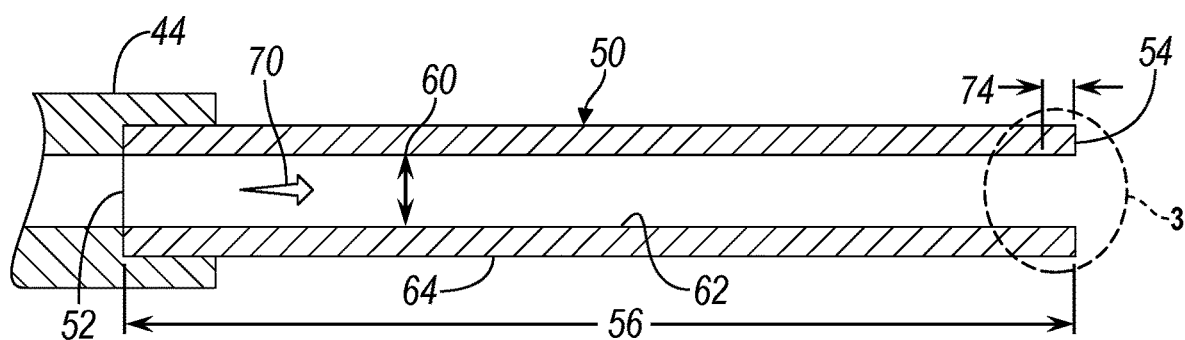
FIG. 2 is a cross-section view of a delivery tube, according to various embodiments.

With continuing reference to FIG. 1 and additional reference to FIG. 2, the delivery tube 50 is illustrated in greater detail. The delivery tube 50 may include a selective length 56 between the proximal end 52 and the distal end 54. The proximal end 52 may be a terminal proximal and the distal end 54 may be a terminal distal end. Therefore, the length 56 may be a complete or total length of delivery tube 50. The length of the delivery tube 50 may be selected based upon one or more various considerations, such as an internal diameter 60 of the delivery tube 50, a material forming the delivery tube 50, a flow rate through the delivery tube 50, and/or other appropriate considerations.

The i.d. 60 may be defined or formed by an internal wall 62 of the delivery tube 50. The i.d. 60 may be any appropriate diameter, such as 0.5 millimeters (mm) to about 5 centimeters (cm). The tube 50 may be further formed of selected materials, such as silica or fused silica, polymers, or the like. In various embodiments the delivery tube 50 may be formed of the fused silica, including at least the interior surface 62 being formed of the fused silica.

The material of the delivery tube 50 generally includes a substantially smooth interior surface 62. The interior surface 62 being substantially smooth includes generally including a surface that is free of defects, such as crevices or other deformations, which are greater than about 2 micrometers (microns), including greater than about 0.02 microns to about 2 microns and further about 0.05 microns or larger. It is understood that the interior surface 62 of the delivery tube 50 may be finished or formed to include crevices or deviations of a size less than or equal to about 0.05 microns. Nevertheless, the delivery tube 50 having the substantially smooth surface may be augmented, as discussed further herein, to include nucleation sites for bubbles that will form and exit the distal end 54 of the delivery tube 50 once nucleated at the nucleation sites, as discussed herein.

As discussed above, the delivery tube 50 is connected to the nozzle 44 to allow material to exit from the container 14 generally in the direction of arrow 70. Accordingly, the delivery fluid 26 enters the delivery tube 50 at the proximal end 52 and travels along the length of the delivery tube 50 in the direction of the arrow 70. The delivery fluid, of at least a portion thereof, engages the interior wall 62 near the distal end 54.

The distal end 54 may include an augmented region 74. The augmented region 74 may extend a distance past the distal end 54, but is not required to do so. The augmented region 74 may include only a distance between the distal end 54 and a distance from the distal end 54 towards the proximal end 52. The length or distance of the augmented region 74 may be any appropriate distance such as about 0.1 microns to about 300 microns, further including about 20 microns to about 200 microns, and further including about 80 microns to about 110 microns. In various embodiments, the augmented region 74 may include the distance that is about 100 microns. It is understood also that the augmented region 74 may include a region that includes only various individual and/or discrete nucleation points for bubbles, but does not need to include an entire surface for the distance 74 that has been augmented in a uniform manner.

Figure 3:
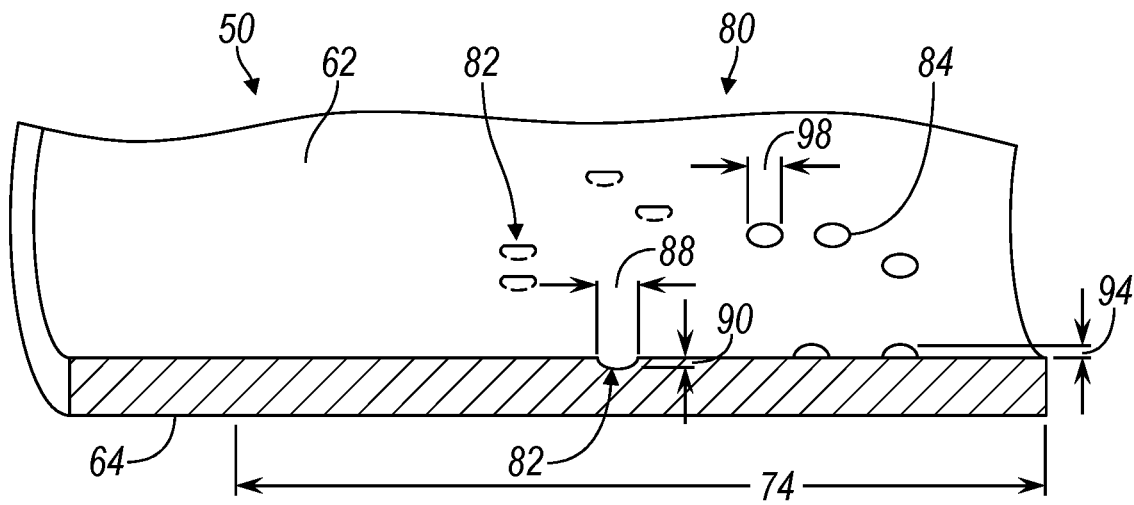
FIG. 3 is a detail cross-section of an augmented region of the delivery tube of FIG. 2.

Continuing reference to FIG. 3, the delivery tube 50, including the internal surface 62 in the augmented region distance 74, may include one or more augmented portions 80. The augmented portions 80 are predetermined or preselected at least generally in size, material, being formed as depressions and/or formed as raised regions, and/or location. The augmented portions 80 may include various features including depressions, such as a pit or crevice 82, which may include a plurality of the pits or crevices 82 in the augmented region 74. In addition to the pits or crevices 82 and/or alternatively thereto, mounds or raised regions 84 may also be formed. The pits 82 and the raised regions 84 may include selected geometries, including dimensions, as discussed further herein. In various embodiments, the augmented portions 80 are individual and discrete portions in the tube 50. The augmented portions 80 need not cover the entire surface area of the augmented region 74 within the tube 50, but only a portion thereof within the augmented region 74.

Further the pits 82 may be formed by sputtering (e.g. removing or destroying) of material from the interior surface 62 of the delivery tube 50. The mounds 84 may be formed by the deposition of material onto the inner surface 62. The sputtering and the deposition of material may be formed by various techniques such as Focused Ion Beam (FIB) processes.

In various embodiments, the pit 82 may include a length 88 that is about 0.05 microns to about 5 microns, and further about 0.05 microns to about 2 microns. The length 88 of the pit 82 may be formed by the FIB according to various known techniques and processes. Further, the pit 82 may include a depth 90 of about 0.05 microns to about 5 microns, and further about 0.05 microns to about 2 microns. It is understood that the pit 82 may be formed by sputtering material from the inner surface 62 of the delivery tube 50 to the selected depth 90 and length 88. It is further understood that the pits 82 may be formed of a selected geometry, such as semi-spherical, semi-oval, or other appropriate shapes. The pits 82 may be formed in the inner surface 62 as concave formations into the inner surface and extend below the inner surface 62 towards an outer surface 64 of the delivery tube 50. Therefore, the pit 82 is formed into the delivery tube 50 such that at the position of the pit 82 the thickness of the delivery tube 50 may be less than an unaltered or unaugmented thickness of the delivery tube 50.

The mounds 84 may be formed by depositing material onto the inner surface 62 of delivery tube 50. The mounds may be formed of any appropriate material, including gallium, gallium alloys, gallium salts, or other appropriate materials. The mounds 84 may include a height dimension 94 of about 0.05 microns to about 5 microns, and further including about 0.05 microns to about 2 microns. It is understood that the height 94 of the mounds 84 discussed above may be a maximum height and that the mounds may be rounded or tapered from an initial or surface height of substantially zero to the height 94. Further, the mounds 84 may be formed in a selected geometry such as including a length or diameter 98. It is understood that the mounds 84 may be substantially semi-spherical, semi-oval, partially spherical, or other appropriate shape. The mounds 84 may be deposited with FIB, accordingly to generally known techniques, on the surface 62 of the tube 50.

According to various embodiments, the mounds 84 may be formed of gallium or gallium alloys that may be used in the FIB processes. As is generally understood in the art, the FIB may have a source of ions, such as a needle or tip 100, illustrated in FIG. 4, to allow for the deposition of material onto the delivery tube 50. The needle 100 may be powered to generate selected ions, such as a charged gallium ion 110. The ion 110 may be focused with a selected focusing mechanism 116 to be directed to a select region, such as to form the crevice 82 and/or the mound 84. The mound 84 may be formed by depositing the ions 110 at a selected energy. The sputtering to form the crevice 82 may be formed by providing the ions 110 at a higher energy to sputter off or etch tube material such that it is ejected or sputtered, as a sputter particle 120. The FIB formed by the ions 110 may be used to form the substantially precisely sized pits 82 and/or mounds 84 in or on the delivery tube 50. The substantially precisely sized pits 82 and the mounds 84 may be repeatedly formed in or on the delivery tube 50 to allow for formation of the bubbles at a selected size and consistency under selected conditions, as discussed further herein.

Figure 4:
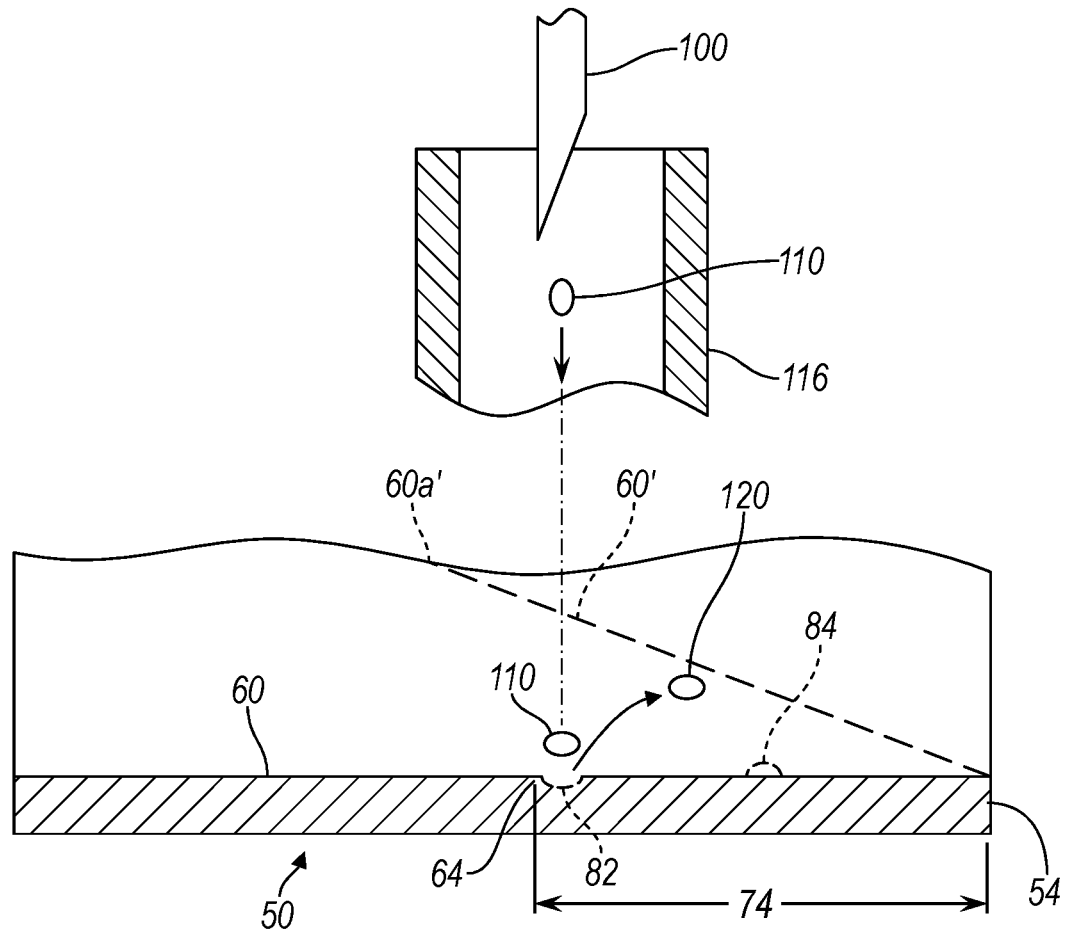
FIG. 4 is a schematic illustration of a formation of selected nucleation sites in the tube.

With continued reference to FIG. 4, the FIB process may engage the inner surface 62 of the tube 50 by positioning the needle 100 relative to the tube 50 and focusing the ions 110 in the beam with the focusing assembly 116. In various embodiments, a portion of the tube 50, such as a portion near the augmented region 70 may be removed to allow access to at least a portion of the internal surface 62. For example, as illustrated in FIG. 4, an angled wall 60' may be formed to extend from the distal end 54 to a proximal portion 60a'. The angled wall 60' may allow access to at least a portion of internal surface 62 of the tube 50 by the ions 110 to form the crevices 82 and/or the mounds 84.

Figure 5:
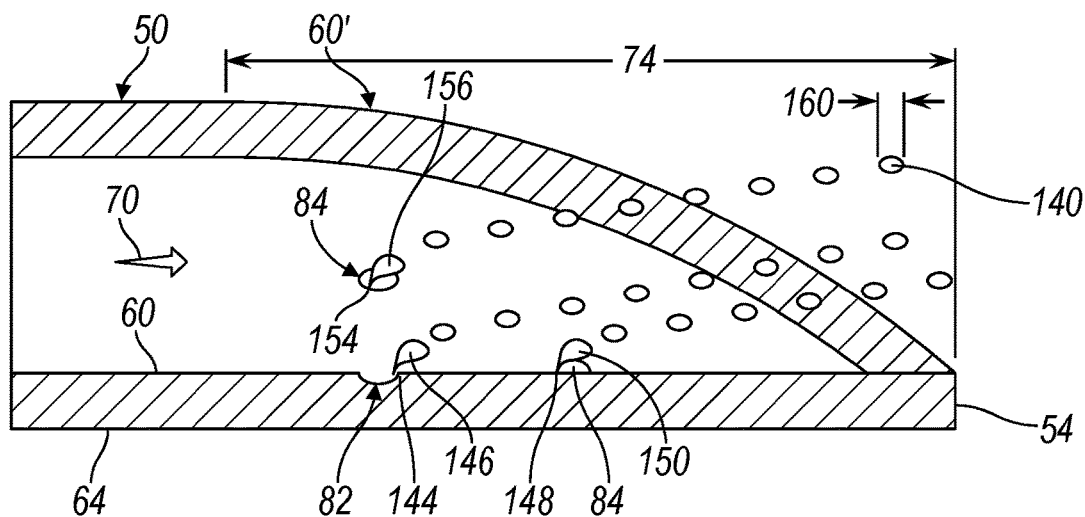
FIG. 5 is a schematic environmental view of delivery of a plurality of bubbles.

With continued reference to FIG. 4 and additional reference to FIG. 5, the delivery tube 50 is connected with the nozzle 44 of the container 14 in the delivery system 10, illustrated in FIG. 1. As illustrated in FIG. 5, the delivery fluid 26 may generally move in the direction of arrow 70. The augmented region 74, including the augmented portions such as the mounds 84 and/or the crevices 82, may form nucleation sites for one or more bubbles 140. The bubbles 140 may nucleate at various regions such as a crevice nucleation region 144 having a bubble nucleating portion 144 having a nucleating bubble 146, a mound interface nucleation region 148 having a nucleating bubble 150, and a mound surface nucleating region 154 having a nucleating bubble 156. Each of the nucleating regions 144, 148, 154 may generate a stream or train of the bubbles 140 to move in the direction of arrow 70 and generally exit the delivery tube 50 near or at the distal end 54. As discussed above, the delivery tube 50 may be augmented to include the slanted or angled wall 60' in at least a portion of the augmented region 74.

Each of the bubbles 140 may be formed and have a final selected size which may be based upon the size of the mound 84 and/or the crevice 82. The size of the bubbles 140 may include an average or maximum diameter dimension 160. The dimension 160 may generally include a diameter of the bubble and may be about 0.01 microns to about 10 microns, further including about 3 microns to about 10 microns, and further about 4.9 microns to about 9.7 microns. Further the diameter 160 may be about 0.01 microns to about 0.2 microns including about 0.09 microns to about 0.15 microns, and further including about 0.09 microns and about 0.012 microns. The bubbles 140 may be formed in the crevices or nucleation site 144 from the crevice 82 that has the length 88.

The delivery fluid 26 may include a super saturated effluent that is flowing at about 10 meters per second through the delivery tube 50. The fluid may include water, such as sterile water, that is saturated with oxygen to 8 bars (116 psi) to about 30 bars (435 psi) for oxygen, including about 20 Bar (about 290 pounds per square inch (psi)). Accordingly, the nucleation sites 144, 148, and 154 may be at a selected portion or in a portion of the crevice of the tube, an interface of the deposited material of the mound 84 and the inner surface 60, or on or within a surface of the mound 84. Nevertheless, the nucleation sites offer the generation of the bubbles 140 at a selected size, as discussed above.

The formation and size limitation of the bubbles 140 may be achieved, according to various embodiments, by forming a laminar flow within the tube 50. The flow rate of the delivery fluid 26 may be within a range to ensure a Reynold's numbers within the tube 50 that is laminar flow. The delivery fluid 26 having a selected, such as a high rate of flow including at rates that ensure laminar flow through the tube 50, therefore shears the nucleating or forming bubble, such as the nucleating bubbles 146, 150, 156. In other words, the bubbles are sheared at a time just after nucleation or initiation of bubble formation to achieve or select a small size (e.g. bubble diameters exiting the tube 50 or just after existing the tube 50 at or about 0.01 microns to about 10 microns in diameter). The sheared bubbles are, therefore, maintained at the small size and are delivered to the host fluid.

Figure 6:
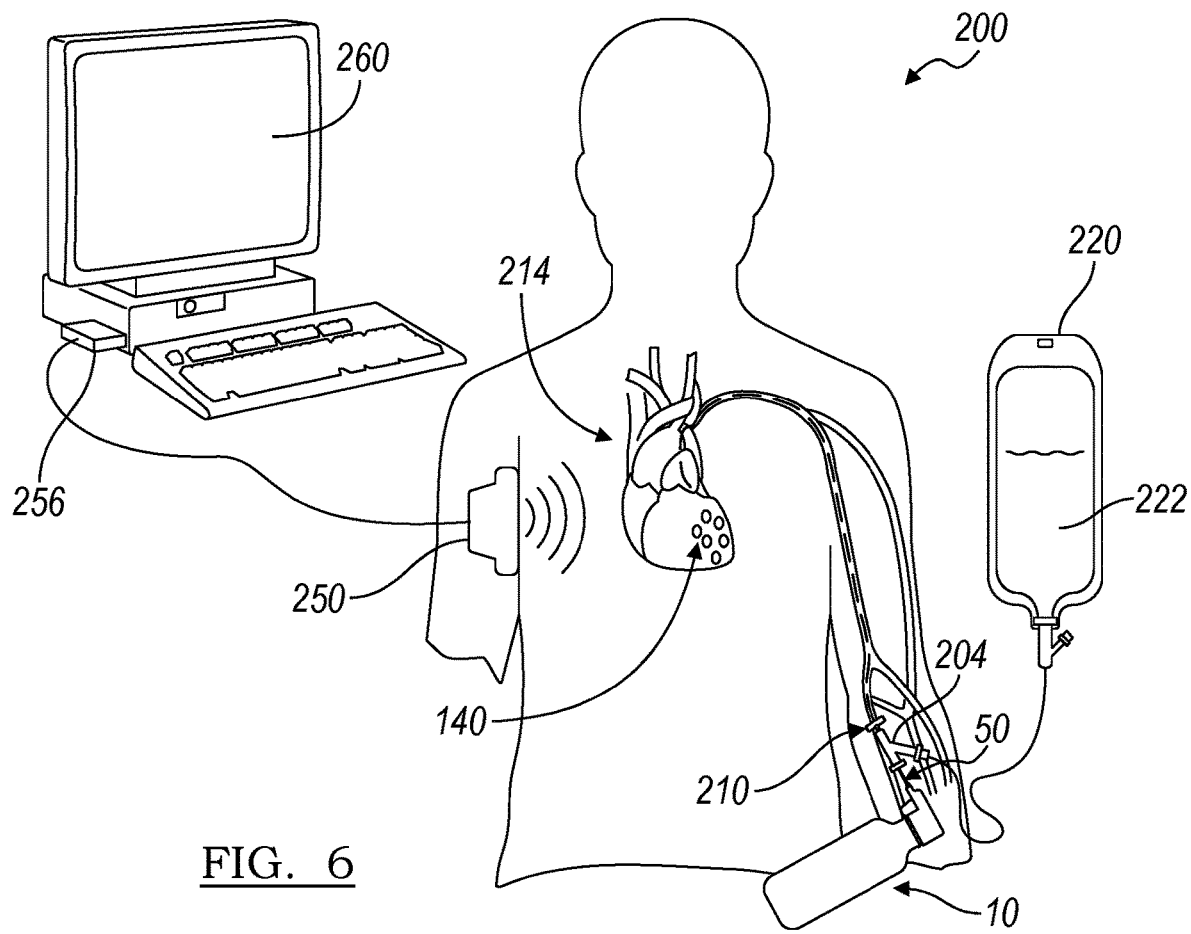
FIG. 6 is an environmental view of a delivery of bubbles for echogenic use.

With reference to FIG. 6, the generated bubbles 140 may be used for various purposes, such as a contrast agent when delivered into a subject, such as a human subject 200. In particular, as discussed above, the container 10 may have the delivery tube 50 connected therewith and may be used to generate the bubbles 140 that are delivered to the subject 100, such as through a valve system 204 that allows access through a venous puncture 210 to a heart 214 of the subject 200. Further, an intravascular (IV) system 220 may include a fluid volume 222 that is also introduced to the subject 200 through the venous puncture through the valve system 204. Therefore, the bubbles 140 generated from the bubble generation system 10 may be carried to the heart 214, such as into a heart chamber.

The generated bubbles 140 may be introduced into a selected volume, such as the patient 200. As an example of delivery, the bubbles 140 may be delivered from the delivery tube 50 into the patient 200 as a single bolus or over a period of time, such as a few seconds. Nevertheless, the volume of the delivery fluid 26 in the container 14 allows bubbles 140 to be generated as desired or selected by a user until the volume 26 is exhausted.

It is further understood, however, that the patient 200 need not be the only receiver of the bubbles 140. Nevertheless, in a human or oxygen metabolizing subject if capillaries in any organ are blocked by oxygen microbubbles, the deoxyhemoglobin binds the oxygen and the tissues metabolize the gas to reverse local ischemia. Thus, the procedure and bubbles 140 produced with substantially or medically pure oxygen product is useful in multiple ways. For example, the bubbles may be generated efficiently with the delivery fluid 26 passing through the delivery tube 50 and into the patient 200, thus allowing a quick bubble generation. This is also simpler, easier, and more rapid than agitating an air and saline mixtures. Further, the device 10 can be used to generate the bubbles 140 in a sterile manner and avoid a potential infection.

An imaging system, such as an ultrasound transducer 250 can be used to acquire images of the heart 214. The bubbles 140 positioned with the volume of the heart 214 can act as a contrast agent for the ultrasound transducer system 250. The ultrasound transducer 250 can be interconnected with an ultrasound imaging system 256, such as the SONOS™ Ultrasound Imaging System sold by Hewlett-Packard, an image can then be displayed on a display device, such as a computer screen 260. The image can be enhanced with the bubbles 140 acting as a contrast agent within the volume of the heart 214 to allow for a clear view of a volume of a heart 214. It is understood that other selected organs of the patient 200 can also be imaged with the ultrasound transducer 250 with the use of the bubbles 140 as a contrast agent. The bubbles 140, as noted above, may be the bubbles 140 formed with the bubble generation system 10 that have been introduced into a selected volume.

In various embodiments, the bubbles may be generated with the system 10 and delivered directly to the patient 200 or subject. Thus, the bubbles may be generated substantially contemporaneously with the introduction or use of the bubbles. Thus, the bubbles need not be formed in a solution and stabilized, such as with other compounds. The bubbles can be formed on demand with the system 10. The bubbles, once introduced, may be used as a contrast agent within the volume being imaged.

It is further understood that an introduction of the bubbles 140 into a human patient 200 is not required. For example, ultrasound imaging can be performed on any appropriate system, such as any mechanism that allows for ultrasound imaging for inspection within a volume. Various examples can include ultrasound inspection of containers, mechanical devices, or other appropriate systems. Accordingly, it is understood by one skilled in the art that introduction of the bubbles 140 into a human subject is not required and that the bubbles can be introduced into any appropriate subject, such as a non-human or non-living subject, for contrast enhancement.

According to various embodiments, the container 10 can include more than one of the tubes 50 interconnected with the nozzle 32. For example, a plurality of the tubes 50 can be positioned substantially parallel to one another to allow for a high volume ejection of a liquid and bubbles from the container 10. The plurality of tubes 50 can be provided in parallel and include the features, as discussed above, including each including the augmented region 74.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

Example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail.

What is claimed is:

1. A system to generate bubbles of a selected size, comprising:
    a container having a volume configured to hold a fluid at a selected pressure;
    a tube having an inner surface and an outer surface and extending from a proximal portion at the container, wherein the tube includes (i) a selected internal diameter defined by the inner surface and (ii) extends to a terminal end at a distal end; and a selected nucleation site formed within the tube from between the terminal end at the distal end and the proximal portion, wherein the selected nucleation site is configured to generate a bubble filled with a gas when the fluid passes the selected nucleation site;

wherein the generated bubbles are operable to be delivered to a host fluid;

wherein the selected nucleation site extends along the inner surface of the tube at an opened access portion of the tube to allow access to the inner surface of the tube that extends from the terminal end to the proximal portion, wherein the opened access is formed by an angled wall of the tube that extends at an acute angle from near the terminal end to the proximal portion;

wherein the opened access portion includes a portion of the tube near the selected nucleation site that is removed to form the angled wall and form the open access;

wherein the open access allows access to at least a portion of the internal surface to an ion beam;

wherein the selected nucleation site includes an ion beam formed pit or crevice in the internal surface or an ion beam deposited material on the internal surface.

2. The system of claim 1, wherein the selected nucleation site is a predetermined nucleation site and includes a plurality of predetermined nucleation sites selected in at least size or material.

3. The system of claim 2, wherein the nucleation region is about 200 microns long.

4. The system of claim 2, wherein the nucleation sites includes at least one of a depression formed in the inner surface of the tube or a mound formed on the inner surface of the tube.

5. The system of claim 1, wherein the selected internal diameter is about 10 microns to about 100 microns.

6. The system of claim 4, wherein the at least one depression is about 0.05 microns to about 5 microns in length.

7. The system of claim 4, wherein the mound is formed to be about 0.05 microns to about 5 microns above a surface of the tube.

8. The system of claim 1, wherein the bubble includes a diameter of about 1 micron to about 10 microns at an exit of the tube.

9. The system of claim 1, further comprising:
a trigger configured to be operated to release the fluid from the container through the tube for generation of the bubbles.

10. The system of claim 9, further comprising:
a receiving port configured to mate with a distal end to the tube to receive the fluid and the bubbles generated in the fluid.

11. A method of generating bubbles with a tube, comprising:
providing a tube having an internal surface with defects having a dimension not greater than about 1 micron;
forming an augmented portion in a nucleation region of the tube, wherein the nucleation region includes interacting with the internal surface with an ion beam or depositing material on the internal surface with the ion beam;
flowing a fluid passed the nucleation region to cause bubbles to nucleate in the augmented portion; and
shearing the bubbles after nucleation with the flowing fluid;
wherein the augmented portion extends along the internal surface of the tube, wherein an opened access portion of the tube extends from a distal terminal end of the tube to a point proximal the distal terminal end formed by an angled wall of the tube formed by a removed portion of the tube;
wherein the opened access portion is near the augmented portion and includes a portion of the tube that is removed to form the angled wall and form the opened access;
wherein the opened access allows access to at least a portion of the internal surface to an ion beam.

12. The method of claim 11, wherein forming the augmented portion includes forming a depression within an internal wall of the tube having a dimension about 0.05 microns to about 5 microns through the opened access portion.

13. A method of generating bubbles with a tube, comprising:
providing a tube having an internal surface with defects having a dimension not greater than about 1 micron;
forming an augmented portion in a nucleation region of the tube;
flowing a fluid passed the nucleation region to cause bubbles to nucleate in the augmented portion;
shearing the bubbles after nucleation with the flowing fluid;
wherein forming the augmented portion includes forming a depression within an internal wall of the tube having a dimension about 0.05 microns to about 5 microns;
wherein forming the depression includes sputtering material with an ion beam through an opened access portion of the tube from the internal surface of the tube on the internal wall to remove material from the internal surface;
wherein the opened access portion is near the augmented portion and includes a portion of the tube that is removed to form the angled wall and form the opened access; and
wherein the augmented portion extends along the opened access portion of the tube from the terminal end of the tube to a point proximal the terminal end that is formed by an angled wall of the tube.

14. The method of claim 11, wherein forming the augmented portion includes forming a mound on an internal wall of the tube through the opened access portion.

15. A method of generating bubbles with a tube, comprising:
providing a tube having an internal surface with defects having a dimension not greater than about 1 micron;
forming an augmented portion in a nucleation region of the tube;
flowing a fluid passed the nucleation region to cause bubbles to nucleate in the augmented portion; and
shearing the bubbles after nucleation with the flowing fluid;
wherein forming the augmented portion includes forming a mound on an internal wall of the tube;
wherein forming the mound on the internal wall includes depositing material on an internal surface of the internal wall through an opened access portion of the tube with focused ion beam deposition;
wherein the augmented portion extends along the opened access portion of the tube from the terminal end of the tube to a point proximal the terminal end that is formed by an angled wall of the tube;

wherein the opened access portion is near the augmented portion and includes a portion of the tube that is removed to form the angled wall and form the opened access.

16. The method of claim 14, wherein forming the mound on the internal wall includes depositing gallium on an internal surface of the internal wall through the opened access portion.

17. The method of claim 14, further comprising:
operating a trigger to cause the flowing of the fluid; and
delivering the generated bubbles to a host fluid.

18. A system to generate bubbles of a selected size, comprising:
a container having a volume configured to hold a fluid at a selected pressure;
a tube extending from the container, wherein the tube includes (i) a selected internal diameter defined by an internal surface, (ii) a terminal end, and (iii) an angled wall extending from the terminal end to a point proximal the terminal end to form an opened access portion to allow open access to a nucleation region within the tube along the angled wall;
a trigger connected to a valve, wherein actuation of the trigger opens the valve to allow release of the fluid from the container through the tube; and
a selected nucleation site formed through the opened access portion within the tube in the nucleation region configured to generate a bubble filled with a gas when the fluid passes the selected nucleation site when released from the container;
wherein the generated bubbles are sheared at the selected nucleation site to achieve a selected size and are operable to be delivered to a host fluid;
wherein the opened access portion includes a portion of the tube near the selected nucleation site that is removed to form the angled wall of the tube and form the opened access;
wherein the opened access allows access to at least a portion of the internal surface to an ion beam;
wherein the selected nucleation site includes an ion beam formed pit or crevice in the internal surface or an ion beam deposited material on the internal surface.

19. The system of claim 18, wherein the selected nucleation site includes at least one of (i) a depression having a length of about 0.05 microns to about 5 microns or (ii) a mound having a height of about 0.05 microns to about 5 microns;
wherein the tube has the selected internal diameter greater than a diameter of the bubbles delivered to the host fluid;
wherein the bubbles delivered to the host fluid have a diameter of about 0.1 microns to about 100 microns.

20. The system of claim 4, wherein the plurality of nucleation sites includes at least one of (i) the depression formed in the internal wall of the tube by removal of a material from the internal wall by sputtering or (ii) the mound formed on the internal wall of the tube by deposition of material with ion beam deposition.

* * * * *

UNITED STATES PATENT AND TRADEMARK OFFICE
CERTIFICATE OF CORRECTION

PATENT NO. : 11,654,205 B2
APPLICATION NO. : 16/754986
DATED : May 23, 2023
INVENTOR(S) : James Richard Spears It is certified that error appears in the above-identified patent and that said Letters Patent is hereby corrected as shown below:

In the Specification

Column 1, Background, Line 37, Delete "Cystolic" and insert --Systolic-- therefor Column 3, Detailed Description, Line 58, Delete "43" and insert --34-- therefor Column 6, Detailed Description, Line 18, Delete "70" and insert --74-- therefor Column 7, Detailed Description, Line 1, Delete "60," and insert --62,-- therefor Column 7, Detailed Description, Line 23, Delete "10" and insert --14-- therefor Column 7, Detailed Description, Line 26, Delete "100," and insert --200,-- therefor Column 7, Detailed Description, Line 41, Delete "26" and insert --222-- therefor Column 8, Detailed Description, Line 28, Delete "10" and insert --14-- therefor Column 8, Detailed Description, Line 30, Delete "32." and insert --44.-- therefor Column 8, Detailed Description, Line 33, Delete "10." and insert --14.-- therefor Signed and Sealed this
Tenth Day of October, 2023

Katherine Kelly Vidal
*Director of the United States Patent and Trademark Office*